(12) United States Patent
Lui et al.

(10) Patent No.: US 8,273,897 B2
(45) Date of Patent: Sep. 25, 2012

(54) METHOD FOR PRODUCING 2,2-DIFLUOROETHYLAMINE DERIVATIVE BY AMIDE HYDROGENATION

(75) Inventors: Norbert Lui, Odenthal (DE); Stefan Antons, Leverkusen (DE)

(73) Assignee: Bayer Cropscience AG, Monhein (DE)

( * ) Notice: Subject to any disclaimer, the term of this patent is extended or adjusted under 35 U.S.C. 154(b) by 270 days.

(21) Appl. No.: 12/677,966

(22) PCT Filed: Sep. 5, 2008

(86) PCT No.: PCT/EP2008/007271
§ 371 (c)(1),
(2), (4) Date: Mar. 12, 2010

(87) PCT Pub. No.: WO2009/036900
PCT Pub. Date: Mar. 26, 2009

(65) Prior Publication Data
US 2010/0222593 A1 Sep. 2, 2010

(30) Foreign Application Priority Data
Sep. 18, 2007 (EP) .................................... 07116640

(51) Int. Cl.
*C07D 213/74* (2006.01)
*C07D 213/61* (2006.01)
*C07D 239/30* (2006.01)
*C07D 237/12* (2006.01)
*C07D 277/32* (2006.01)

(52) U.S. Cl. ......... 546/329; 544/224; 544/334; 548/205

(58) Field of Classification Search .................. 546/329; 544/334, 224; 548/205
See application file for complete search history.

(56) References Cited

U.S. PATENT DOCUMENTS

| | | | | |
|---|---|---|---|---|
| 2,691,043 | A * | 10/1954 | Husted et al. .................. | 564/488 |
| 2009/0253749 | A1 | 10/2009 | Jeschke et al. | |
| 2010/0048646 | A1* | 2/2010 | Jeschke et al. ................ | 514/357 |
| 2010/0240705 | A1 | 9/2010 | Jeschke et al. | |

FOREIGN PATENT DOCUMENTS

| | | |
|---|---|---|
| EP | 0 694 523 | 1/1996 |
| JP | 2007/284352 | 11/2007 |
| WO | 2006/013939 A | 2/2006 |
| WO | 2007/115644 A1 | 10/2007 |
| WO | 2007/115646 A1 | 10/2007 |
| WO | WO 2008009360 A2 * | 1/2008 |

OTHER PUBLICATIONS

Tafesh, Ahmed M.; Weiguny, Jens "A Review of the Selective Catalytic Reduction of Aromatic Nitro Compounds into Aromatic Amines, Isocyanates, Carbamates, and Ureas Using CO" Chem. Rev. 1996, 96, 2035-2052.*
Fieser and Fieser, Reagents for Organic Synthesis, vol. 1 Wiley: NY, 1974, p. 726.*
Lithium Aluminum Hydride Paquette, L. in Encyclopedia of Reagents for Organic Synthesis Online Posting Date: Oct. 15, 2004 2004 John Wiley & Sons, Ltd. http://www.mrw.interscience.wiley.com/eros/articles/r1036/frame.html.*
Amundsen, L.H. et. al. J. Am. Chem. Soc. 1951, 73, 242-244.*
Hutchins, R.O. et. al. J. Org. Chem. 1977, 42, 82-91.*
Fernandes "Reduction of amides with silanes catalyzed by MoO2CI2" Journal of Molecular Catalysis A: Chemical 2007, 272, 60-63.*
Yamanaka "Reduction of Amides Containing Polyfluoroalkyl Groups" Nippon Kagaku Kaishi, 1987 (10), 1796-801 (with English reaction summary).*
S. Patai; "The Chemistry of Amino Group;" Interscience Publishers; New York; 1968.
Dedek et al.; "Journal of Fluorine Chemistry;" 1986; 31; 363-379.
Kuwano et al.; "Reduction of Amides to Amines Via Catalytic Hydrosilylation by a Rhodium Complex;" Tetrahedron Letters; 1998; 39; pp. 1017-1020.
International Search Report Based on PCT/EP2008/007271 Mailed Feb. 5, 2009.
Database Beilstein, Beilstein Institute for Organic Chemistry, Frankfurt, Main, Germany; Jan. 19, 2009; Patent Chemistry Databse: Copyright 2007-2008; Elsevier Inc.; XP-002511025.
European Search Report based on European Application No. PCT/EP2008/007271 dated Feb. 5, 2009.
International Search Report based on Application No. PCT/EP2008/007271 dated Feb. 5, 2009.

* cited by examiner

*Primary Examiner* — David K O'Dell
(74) *Attorney, Agent, or Firm* — Bayer Donelson Bearman, Caldwell & Berkowitz, PC

(57) ABSTRACT

Process for preparing 2,2-difluoroethylamine derivatives, wherein compounds of the general formula (IV) are reduced to the corresponding 2,2-difluoroethylamine derivatives of the general formula (III), where the A radical is as defined in the description:

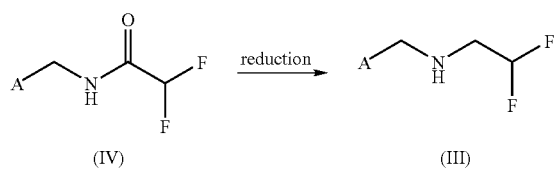

7 Claims, No Drawings

METHOD FOR PRODUCING 2,2-DIFLUOROETHYLAMINE DERIVATIVE BY AMIDE HYDROGENATION

CROSS REFERENCE TO RELATED APPLICATIONS

This application is a §371 National Stage Application of PCT/EP2008/007271 filed Sep. 5, 2008, which claims priority to European Application 07116640.9 filed Sep. 18, 2007.

BACKGROUND OF THE INVENTION

1. Field of the Invention

The present invention relates to a process for preparing 2,2-difluoroethylamine derivatives proceeding from 2,2-difluoroacetamide derivatives. The present invention further provides the 2,2-difluoroacetamide derivatives used as starting compounds in this process according to the invention, the preparation thereof and the use thereof for preparing 2,2-difluoroethylamine derivatives.

2. Description of Related Art

Derivatives of 2,2-difluoroethylamines are important intermediates for preparing active agrochemical ingredients. Appropriate 2,2-difluoroethylamine derivatives can be used, for example, in the synthesis of insecticidally active enaminocarbonyl compounds, for example of 4-aminobut-2-enolide compounds. Enaminocarbonyl compounds which contain 2,2-difluoroethylamino units are known, for example, from International Patent Applications WO 2007/115644 and WO 2007/115646.

WO 2007/115644 discloses that 2,2-difluoroethylamine derivatives, for example the compound of the formula (IIIa) below, can be prepared by alkylating the amine of the formula (Ia) with optionally substituted chloromethylpyridine of the formula (IIa) (scheme 1 of WO 2007/115644; cf. preparation of starting compounds; compounds of the formula (III); III-1: N-[(6-chloropyridin-3-yl)methyl]-2,2-difluoroethyl-1-amine).

Scheme 1:

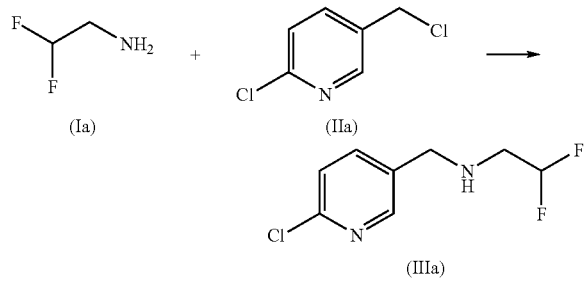

A disadvantage in this process is the low yield of 53%, which is caused by the possible polyalkylation of the nitrogen atom. This proportion of polyalkylation can only be reduced through the use of a large excess of amine, which is, though, uneconomic in the case of a costly amine.

SUMMARY OF THE INVENTION

Proceeding from this prior art, it is an object of the present invention to provide a process for preparing 2,2-difluoroethylamine derivatives, which is preferably simple and inexpensive to perform. The 2,2-difluoroethylamine derivatives obtainable by this desired process should preferably be obtained with high yield and high purity. More particularly, the desired process should enable the desired target compounds to be obtained without the need for complex purification methods.

This object is achieved by a process for preparing 2,2-difluoroethylamine derivatives.

The process according to the invention is characterized in that 2,2-difluoroacetamide derivatives of the general formula (IV) are reduced to the corresponding target compounds of the general formula (III) according to the following scheme 2:

Scheme 2:

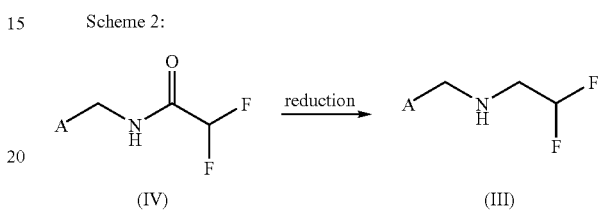

DETAILED DESCRIPTION OF A PREFERRED EMBODIMENT

The invention thus envisages that the desired 2,2-difluoroethylamine derivatives of the general formula (III) are prepared by a reduction of the corresponding 2,2-difluoroacetamide derivatives of the general formula (IV). The desired 2,2-difluoroethylamine derivatives of the general formula (III) are obtained under the inventive reaction conditions and preferred reaction conditions specified in detail below with good yields in high purity, as a result of which the process according to the invention overcomes the abovementioned disadvantages. The desired compounds are obtained in a purity which generally does not necessitate an extensive workup of the direct reaction product. Compared to the process known from the prior art, which proceeds from an amine to be alkylated according to scheme 1, the yields can be improved by the process according to the invention.

In the context of the present invention, a derivative refers to a similar structure derived from the organic base structure (unit) in question, i.e. a 2,2-difluoroethylamine derivative is understood to mean, for example, a compound which includes a 2,2-difluoroethylamine unit.

In the abovementioned general formulae (III) and (IV), the A radical is defined as follows:

pyrid-2-yl or pyrid-4-yl, or pyrid-3-yl which is optionally 6-substituted by fluorine, chlorine, bromine, methyl, trifluoromethyl or trifluoromethoxy, or pyridazin-3-yl which is optionally 6-substituted by chlorine or methyl, or pyrazin-3-yl, or 2-chloropyrazin-5-yl, or 1,3-thiazol-5-yl which is optionally 2-substituted by chlorine or methyl, or pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl, which is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine), or $C_1$-$C_3$-alkylsulphonyl (which is optionally substituted by fluorine and/or chlorine), or

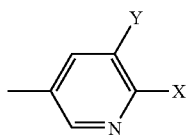

in which

X is halogen, alkyl or haloalkyl and

Y is halogen, alkyl, haloalkyl, haloalkoxy, azido or cyano.

Preferred, particularly preferred and very particularly preferred definitions of the A radical shown in the abovementioned general formulae (III) and (IV) are elucidated below.

A is preferably selected from the group consisting of 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl and 5-difluoromethyl-6-iodopyrid-3-yl.

A is more preferably selected from the group consisting of 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl and 5-difluoromethyl-6-chloropyrid-3-yl.

A is most preferably selected from the group consisting of 6-chloropyrid-3-yl, 6-bromopyrid-3-yl, 6-chloro-1,4-pyridazin-3-yl, 5-fluoro-6-chloropyrid-3-yl and 5-fluoro-6-bromopyrid-3-yl.

The term "alkyl", either alone or in combination with further terms, for example haloalkyl, is understood in the context of the present invention to mean a radical of a saturated, aliphatic hydrocarbon group having 1 to 12 carbon atoms, which may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, $C_1$-$C_6$-alkyl radicals are particularly preferred. $C_1$-$C_4$-Alkyl radicals are especially preferred.

According to the invention, the term "aryl" is understood to mean an aromatic radical having 6 to 14 carbon atoms, preferably phenyl.

The term "arylalkyl" is understood to mean a combination of "aryl" and "alkyl" defined in accordance with the invention, the radical generally being bonded via the alkyl group; examples thereof are benzyl, phenylethyl or α-methylbenzyl, particular preference being given to benzyl.

In the context of the present invention, halogen-substituted radicals, for example haloalkyl, are understood to mean radicals halogenated once or more than once up to the maximum possible number of substituents. In the case of polyhalogenation, the halogen atoms may be the same or different. Halogen represents fluorine, chlorine, bromine or iodine, especially fluorine, chlorine or bromine.

The term "alkoxy", either alone or in combination with further terms, for example haloalkoxy, is understood in the present context to mean an O-alkyl radical, where the term "alkyl" is as defined above.

Optionally substituted radicals may be mono- or polysubstituted, where the substituents may be the same or different in the case of polysubstitution.

The 2,2-difluoroacetamide derivatives of the general formula (IV) can be reduced to the corresponding amines of the general formula (III) with reducing agents known per se to those skilled in the art. For example, it is possible to perform the reduction with complex hydrides, non-complex metal or semimetal hydrides, hydrides of silicon compounds of the general formula

where $R^3$ is H, optionally substituted alkyl, optionally substituted aryl or chlorine, or by catalytic hydrogenation.

Complex hydrides are generally understood to mean charged metal complexes which contain at least one hydride ligand. Examples thereof are lithium aluminium hydride (LiAlH$_4$). LiAAlH(O-tert-butyl)$_3$, LiAlH(O-methyl)$_3$, NaAlEt$_2$H$_2$ and the like. Examples of non-complex metal and semimetal hydrides are boranes, such as BH$_3$, 9-BBN (9-borabicyclo[3.3.1]nonane) and disiamylborane, AlH$_3$, DIBAL-H (AlH(isobutyl)$_2$) and the like.

Borane (BH$_3$) can be used in gaseous form (as diborane B$_2$H$_6$) or in solution (e.g. as an etherate in the form of BH$_3$ complexes, such as BH$_3$.THF or BH$_3$.Me$_2$S or BH$_3$.pyridine). When borohydrides are used, they can also be obtained in situ. For example, borohydrides can be obtained in situ by reacting hydridic boron salts, such as LiBH$_4$, NaBH$_4$ or KBH$_4$, with Lewis or Brønsted acids or halogens, such as iodine, bromine or chlorine.

Examples of suitable Lewis acids are boron halides, aluminium halides or iron halides.

Examples of suitable Brønsted acids are H$_2$SO$_4$, HCl or phosphoric acid. Equally, the borohydrides can be obtained by reacting boron halides, such as BF$_3$, BCl$_3$ or BBr$_3$, with complex hydrides, such as NaH or LiAlH$_4$.

The amine-borane complexes which are formed first in this case can be converted to the free amines either by addition of a suitable acid or by addition of a base. Suitable acids may, for example, be aqueous hydrochloric acid, sulphuric acid and phosphoric acid. Suitable bases are, for example, sodium hydroxide solution, potassium hydroxide solution and aqueous ammonia. The acids or bases used are used in excess. Preference is given to amounts of 1.5 to 2 equivalents. The temperatures can be varied within a wide range. Preference is given to temperatures between 0° C. and 40° C. The pH can be varied between 0 and 14 during the amine release. In the case of acidic cleavage, a pH of 5 to 2 is preferred. In the case of basic cleavage, a pH von 8 to 12 is preferred.

In the case of reduction with silicon hydrides, it is possible, for example, to use noble metal catalysts such as rhodium salts or noble metal complexes. Corresponding procedures are described in Tetrahedron Letters, 39 (1998), pages 1017 to 1020.

When a catalytic hydrogenation is employed to reduce the compound of the general formula (IV), the catalyst used may be any hydrogenation catalyst. Examples of useful catalysts include palladium catalysts, platinum catalysts, Raney nickel catalysts, Lindlar catalysts and rhodium catalysts. As well as these heterogeneous catalysts, it is also possible, however, to carry out hydrogenations over homogeneous catalysts, for example over the Wilkinson catalyst.

The catalytic hydrogenation can be carried out under reduced pressure in an autoclave or in a hydrogen gas atmosphere under standard pressure. The hydrogen gas atmosphere may additionally comprise inert gases, for example argon or nitrogen.

In general, it is advantageous to perform the process according to the invention in the presence of solvents (diluents). Solvents are advantageously used in such an amount that the reaction mixture remains efficiently stirrable over the entire reduction process. Useful solvents for performing the process according to the invention include all organic solvents which are inert under the reaction conditions, the type of solvent used depending on the way in which the reduction is performed, i.e. more particularly on the type of reducing agent.

Examples include: halohydrocarbons, especially chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, methyl n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, dioxane, dichlorodiethyl ether and polyethers of ethylene oxide and/or of propylene oxide; amines such as trimethyl-, triethyl-, tripropyl-, tributylamine, N-methylmorpholine, pyridine, alkylated pyridines and tetramethylenediamine; compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons such as pentane, hexane, heptane, octane, nonane and technical hydrocarbons which may be substituted by fluorine and chlorine atoms, such as methylene chloride, dichloromethane, trichloromethane, carbon tetrachloride, fluorobenzene, chlorobenzene or dichlorobenzene; for example so-called white spirits comprising components with boiling points in the range, for example, of 40° C. to 250° C., cymene, petroleum fractions within a boiling range of 70° C. to 190° C., cyclohexane, methylcyclohexane, petroleum ether, ligroin, octane, benzene, toluene, chlorobenzene, bromobenzene, xylene; esters such as methyl acetate, ethyl acetate, butyl acetate, isobutyl acetate, and dimethyl carbonate, dibutyl carbonate or ethylene carbonate.

Among the aforementioned solvents, THF or THF/toluene mixtures are preferred.

The amounts of solvent used may be varied within a wide range. In general, amounts of solvent in the range of 1 to 50 times the amount of solvent, more preferably of 2 to 40 times the amount of solvent, especially of 2 to 30 times the amount of solvent, based in each case on the substituted 2,2-difluoroacetamide of the general formula (IV) used, are used.

In a further embodiment of the process according to the invention, it is possible to work without solvent in the melt of the 2,2-difluoroacetamide derivative of the general formula (IV) used as the reactant.

The reduction is effected generally under those reaction conditions (pressure, temperature, stoichiometry etc.) under which the carbonyl group is reduced to the $CH_2$ group, but the other functional groups present in the molecule simultaneously remain unchanged.

Preferred reaction temperatures for the reduction with complex hydrides range from −20° C. to 100° C., preference being given to temperatures of 0 to 30° C. The reductions can be effected at standard pressure or else under elevated pressures down to 200 bar. Especially at higher reaction temperatures, it may be helpful also to work at elevated pressures in an autoclave. It is also possible to carry out an additional pressure increase by means of an additional inert gas, such as nitrogen or argon.

In a preferred embodiment of the process according to the invention, the hydrogenation is effected under standard pressure at room temperature.

The reducing agent used is used in a generally 1.1- to 5-fold molar excess, more preferably a 1.3- to 4-fold molar excess, especially a 1.5- to 3-fold molar excess, based in each case on the 2,2-difluoroacetamide derivative of the general formula (IV) used.

The reaction time of the hydrogenation is generally 30 minutes to 24 hours, though longer reaction times do not have an adverse effect.

When catalysts are used, their amount can be varied from 0.01 to 10 per cent by weight, based on the substituted 2,2-difluoroacetamide of the general formula (IV) used.

The workup and purification can be effected via the free amine, via the amine-borane complexes or via salts of the amine. The free amine is preferably isolated by extractions and subsequent distillation. In the case of amine salts, for example of salts of the organic or inorganic acids, purification is effected preferably by crystallization. Preferred salts are, for example, hydrochlorides or acetates. Water-soluble salts can be purified by extracting the aqueous solutions. The amine can then finally be released from its salts by reaction with organic or inorganic bases. Preferred bases are $NaHCO_3$, $Na_2CO_3$ or NaOH.

The present invention additionally also relates to the use of the compounds of the general formula (IV) to prepare compounds of the general formula (III), as disclosed in the process described above.

The compounds of the general formula (IV) required for the inventive reaction can be obtained by reacting compounds of the general formula (VI)

(VI)

in which
$R^1$ is halogen, O-alkyl, O-alkylaryl or aryl
with amines of the general formula (VII)

(VII)

in which A is as defined above to give a compound of the general formula (IV)

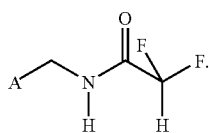

(IV)

The compounds of the general formula (VI) required for this reaction are commercially available or can be prepared by literature methods (Journal of Fluorine Chemistry, 31(4), 363-79, 1986; EP 0 694 523 A; Jpn. Kokai Tokkyo Koho, 11343267).

In the compound of the general formula (VI), $R^1$ is generally halogen, O-alkyl or O-arylalkyl. $R^1$ is preferably Cl, F, O—$C_1$-$C_6$-alkyl, more preferably OEt, OMe or Cl.

The amines of the general formula (VII) required for the conversion to the compound of the general formula (IV) are commercially available or can be prepared by literature methods (cf., for example, S. Patai "The Chemistry of Amino Group", Interscience Publishers, New York, 1968).

The reaction to prepare the compounds of the general formula (IV) is generally carried out in such a way that the difluoroacetic acid derivative of the general formula (VI) is initially charged and then reacted with the corresponding amine of the general formula (VII). The reaction can be carried out at a temperature of generally 0 to 150° C., in particular 20 to 130° C., especially 20 to 110° C. In a particularly preferred embodiment, this reaction which leads to the compounds of the general formula (IV) is carried out without the addition of a solvent, i.e. the difluoroacetic acid derivative of the general formula (VI) is initially charged and simultaneously used as the solvent.

The compound $HR^1$ formed in this reaction—for example EtOH when the compound of the general formula (VI) used is an ethyl ester—can be removed from the crude product easily, for example by distillation.

The reaction to prepare the amides of the general formula (N) can additionally also be carried out in the presence of solvents (diluents). In this process step too, the solvents are preferably also used in such an amount that the reaction mixture remains efficiently stirrable over the entire process. Useful solvents for performing the process according to the invention for preparing the 2,2-difluoroamide derivatives of the general formula (VI) include all organic solvents which are inert under the reaction conditions.

Examples include: halohydrocarbons, especially chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers such as ethyl propyl ether, methyl tert-butyl ether, methyl n-butyl ether anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, dioxane, dichlorodiethyl ether and polyethers of ethylene oxide and/or of propylene oxide; amines such as trimethyl-, triethyl-, tripropyl-, tributylamine, N-methylmorpholine, pyridine, alkylated pyridines and tetramethylenediamine; nitrohydrocarbons such as nitromethane, nitroethane, nitropropane, nitrobenzene, chloronitrobenzene, o-nitrotoluene; nitriles such as acetonitrile, methyl nitrite, propionitrile, butyronitrile, isobutyronitrile, benzonitrile, phenyl nitrile, m-chlorobenzonitrile, and compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons such as pentane, hexane, heptane, octane, nonane and technical hydrocarbons which may be substituted by fluorine and chlorine atoms, such as methylene chloride, dichloromethane, trichloromethane, carbon tetrachloride, fluorobenzene, chlorobenzene or dichlorobenzene; for example so-called white spirits comprising components with boiling points in the range, for example, of 40° C. to 250° C., cymene, petroleum fractions within a boiling range of 70° C. to 190° C., cyclohexane, methylcyclohexane, petroleum ether, ligroin, octane, benzene, toluene, chlorobenzene, bromobenzene, nitrobenzene, xylene; esters such as methyl acetate, ethyl acetate, butyl acetate, isobutyl acetate, and dimethyl carbonate, dibutyl carbonate or ethylene carbonate; amides such as hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2 (1H)-pyrimidine, octylpyrrolidone, octylcaprolactam, 1,3-dimethyl-2-imidazolinedione, N-formylpiperidine, N,N'-1, 4-diformylpiperazine; ketones such as acetone, acetophenone, methyl ethyl ketone, methyl butyl ketone. Among the aforementioned solvents, toluene is especially preferred.

The present invention further additionally provides compounds of the general formula (IV) which are used as intermediates in the preparation of the target compounds of the general formula (III):

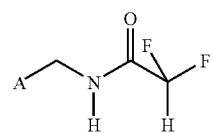

(IV)

In these intermediates, the substituent A is generally defined as follows:
pyrid-2-yl or pyrid-4-yl, or pyrid-3-yl which is optionally 6-substituted by fluorine, chlorine, bromine, methyl, trifluoromethyl or trifluoromethoxy, or pyridazin-3-yl which is optionally 6-substituted by chlorine or methyl, or pyrazin-3-yl, or 2-chloropyrazin-5-yl, or 1,3-thiazol-5-yl which is optionally 2-substituted by chlorine or methyl, or
pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl, which is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine), or $C_1$-$C_3$-alkylsulphonyl (which is optionally substituted by fluorine and/or chlorine), or

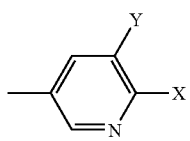

in which

X is halogen, alkyl or haloalkyl and is halogen, alkyl, haloalkyl, haloalkoxy, azido or cyano.

Preferred, particularly preferred and very particularly preferred substituents or ranges of the A radical shown in the abovementioned general formulae (III) and (IV) are elucidated below, A is preferably selected from the group consisting of 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl and 5-difluoromethyl-6-iodopyrid-3-yl.

A is more preferably selected from the group consisting of 6-fluoropyrid-3-yl, 6-chloropyrid-3-yl, 6-bromopyrid-3-yl, 6-chloro-1,4-pyridazin-3-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl and 5-difluoromethyl-6-chloropyrid-3-yl.

A is most preferably selected from the group consisting of 6-chloropyrid-3-yl, 6-bromopyrid-3-yl, 6-chloro-1,4-pyridazin-3-yl, 2-chloro-1,3-thiazol-5-yl, 5-fluoro-6-chloropyrid-3-yl and 5-fluoro-6-bromopyrid-3-yl.

The compounds of the general formula (IV) can be used as reactants to prepare 2,2-difluoroamide derivatives of the general formula (IV).

Proceeding from the compounds of the general formula (III) which are obtained by the process according to the invention, it is possible to prepare insecticidally active enaminocarbonyl compounds which include 2,2-difluoroethylamino units and are described, for example, in international patent applications WO 2007/115644 and WO 2007/115646.

For this purpose, the compounds of the general formula (III)

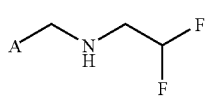
(III)

can be alkenylated on the secondary amine nitrogen, for example by reaction with tetronic acid or derivatives thereof.

A corresponding reaction is described in detail in scheme I of WO 2007/115644 and leads directly to the insecticidally active enaminocarbonyl compounds.

The present invention is illustrated in detail by the examples which follow, though the examples should not be interpreted in a limiting manner.

PREPARATION EXAMPLES

Example 1

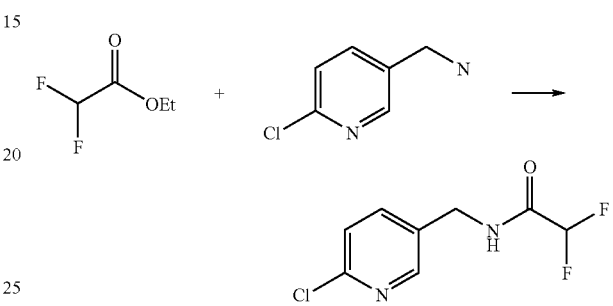

An initial charge of 124 g (1 mol) of ethyl 1,1-difluoroacetate is admixed with 142.6 g of 2-chloro-5-aminomethylpyridine. The reaction mixture is heated to 100° C. and boiled under reflux for one hour. After the cooling has been switched off, the ethanol formed is distilled over. Towards the end of the reaction, to fully remove the ethanol, the mixture is heated up to a bottom temperature of 115° C. or a gentle vacuum is applied. In the reaction flask, there remain 221 g of 99% amide (99% of theory), which solidifies at about 90° C.

NMR (d-DMSO): NH (br s, 9.4 ppm); 1H (s, 8.35 ppm); 1H (d, 7.75 ppm); 1H (d, 7.5 ppm); 1H (t, 6.1-6.4 ppm); 2H (s, 4.4 ppm).

Example 2

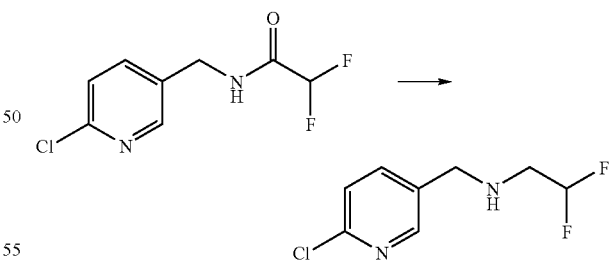

22.6 g (0.1 mol) of N-(2-chloro-5-aminomethylpyridine)-1,1-difluoroacetamide are initially charged in 200 ml of THF after addition of 1 g of RhCl$_3$.3 H$_2$O. Then 21 g of phenylsilane are added and stirring is continued until conversion is complete. Thereafter, the mixture is admixed with 1 N hydrochloric acid and extracted with diethyl ether. The aqueous phase is alkalized with 15% sodium hydroxide solution and extracted with diethyl ether. After drying over Na$_2$SO$_4$, the solvent is distilled off under reduced pressure. There remain 20 g of 98% amine (95% of theory).

NMR(d-DMSO): 1H (s, 8.35 ppm); 1H (d, 7.8 ppm); 1H (d, 7.46 ppm); 1H (td, 6.02 ppm); 2H (s, 3.8 ppm); 2H (td, 2.9 ppm)

Example 3

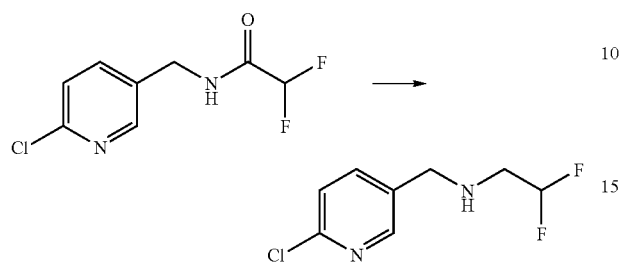

20 g (0.091 mol) of N-(2-chloro-5-aminomethylpyridine)-1,1-difluoroacetamide are initially charged in 200 ml of THF. After the addition of 6.86 g of NaBH$_4$, the mixture is cooled to 0 to 5° C., and 34.3 g of BF$_3$.etherate are added dropwise. The mixture is stirred at 0 to 5° C. overnight. For workup, ethanol and then dilute hydrochloric acid are added dropwise, and the mixture is stirred for a few more hours. After the majority of THF has been distilled off under reduced pressure, the water phase is extracted with ether. The aqueous phase is adjusted to pH 12 with 15% sodium hydroxide solution and extracted twice with diethyl ether. After drying over Na$_2$SO$_4$, the solvent is distilled off under reduced pressure. There remain 17.75 g of 95% amine (90% of theory).

NMR data: see Example 2

Example 4

20 g (0.091 mol) of N-(2-chloro-5-aminomethylpyridine)-1,1-difluoroacetamide are initially charged in 200 ml of THF. After the addition of 6.86 g of NaBH$_4$, the mixture is cooled to 0 to 5° C., and 34.3 g of BF$_3$.etherate are added dropwise. The mixture is stirred at 0 to 5° C. overnight. For workup, ethanol and then dilute sodium hydroxide solution are added dropwise, and the mixture is stirred at 40° C. for a few more hours. The pH of the solution is 12. After the majority of THF has been distilled off under reduced pressure, the water phase is extracted twice with diethyl ether. After drying over Na$_2$SO$_4$, the solvent is distilled off under reduced pressure. There remain 17 g of 95% amine (86% of theory).

The invention claimed is:

1. A process for preparing a 2,2-difluoroethylamine derivative, comprising reducing a 2,2-difluoroacetamide derivative of formula (IV) to the corresponding 2,2-difluoroethylamine derivative of formula (III):

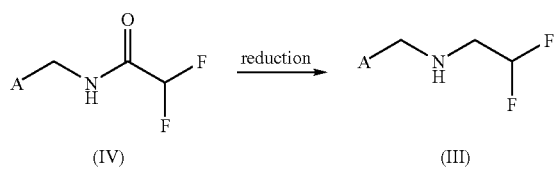

by using a reducing agent which is selected from LiAlH$_4$, LiAlH(O-tert-butyl)$_3$, LiAlH(O-methyl)$_3$, NaAlEt$_2$H$_2$, borohydrides, BH$_3$, 9-borabicyclo[3.3.1]nonane, disiamylborane, AlH$_3$, DIBAL-H (AlH(isobutyl)$_2$), or hydrides of silicon hydrides of the formula

where R—is H, optionally substituted alkyl, optionally substituted phenyl or chlorine; and where the A radical in formulae (III) and (IV) is 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl or 5-difluoromethyl-6-iodopyrid-3-yl.

2. The process according to claim 1, wherein the A radical in formula (IV) and (III) is 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl.

3. The process according to claim 1, wherein the A radical in formula (IV) and (III) is 6-chloropyrid-3-yl, 6-bromopyrid-3-yl, 6-chloro-1,4-pyridazin-3-yl, 2-chloro-1,3-thiazol-5-yl, 5-fluoro-6-chloropyrid-3-yl or 5-fluoro-6-bromopyrid-3-yl.

4. The process according to claim 1, wherein the reducing agent is a borohydride, in gaseous form or in solution.

5. The process according to claim 1, wherein the reducing agent is borohydride, which is prepared in situ by reacting (i) hydridic boron salt with a Lewis acid, Brønsted acid, iodine, bromine or chlorine or (ii) boron halide with NaH or LiAlH$_4$, wherein the hydridic boron salt is selected from the group consisting of LiBH$_4$, NaBH$_4$ and KBH$_4$, the Lewis acid is selected from the group consisting of boron halide, aluminium halide and iron halide, the Brønsted acid is selected from the group consisting of H$_2$SO$_4$, HCl and phosphoric acid, and the boron halide is selected from the group consisting of BF$_3$, BCl$_3$ and BBr$_3$.

6. The process according to claim 1, wherein the silicon hydrides of the formula H—Si—R$_3$ are used together with noble metal catalysts selected from the group consisting of rhodium salts and noble metal complexes.

7. The process according to claim 1, wherein the A radical in formula (IV) and (III) is 6-chloropyrid-3-yl.

* * * * *